United States Patent
Yokobori et al.

(10) Patent No.: US 10,457,762 B2
(45) Date of Patent: Oct. 29, 2019

(54) DIACRYLATE COMPOUND, COMPOSITION THEREOF, AND CURED PRODUCT THEREOF

(71) Applicant: MITSUBISHI GAS CHEMICAL COMPANY, INC., Chiyoda-ku (JP)

(72) Inventors: Umi Yokobori, Niigata (JP); Taketo Ikeno, Niigata (JP); Hideyuki Sato, Niigata (JP); Tomoo Tsujimoto, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 15/322,031

(22) PCT Filed: Jul. 2, 2015

(86) PCT No.: PCT/JP2015/069207
§ 371 (c)(1),
(2) Date: Dec. 23, 2016

(87) PCT Pub. No.: WO2016/002909
PCT Pub. Date: Jan. 7, 2016

(65) Prior Publication Data
US 2017/0129980 A1    May 11, 2017

(30) Foreign Application Priority Data
Jul. 2, 2014 (JP) ................. 2014-137107

(51) Int. Cl.
*C08F 220/28* (2006.01)
*C08F 20/28* (2006.01)
(Continued)

(52) U.S. Cl.
CPC ........ *C08F 222/1006* (2013.01); *C07C 67/03* (2013.01); *C07C 67/08* (2013.01);
(Continued)

(58) Field of Classification Search
CPC .... C08F 222/1006; C08F 220/28; C08F 2/50; C08F 20/28; C08F 222/1013; C09D 7/40;
(Continued)

(56) References Cited

U.S. PATENT DOCUMENTS 3,287,419 A    11/1966 Duke, Jr. et al.
4,287,330 A *   9/1981 Rich .................... C09J 4/00
                                                523/176
(Continued)

FOREIGN PATENT DOCUMENTS

JP    49-52283 A    5/1974
JP    1-221348 A    9/1989
(Continued)

OTHER PUBLICATIONS

Antonio Bello, et al., "Thermotropic Liquid Crystal Polyesters Derived From 4.4'-Biphenyldicarboxylic Acid and Oxyalkylene Spacers", Macromolecular Symposia, vol. 84, pp. 297-306, (1994).

(Continued)

*Primary Examiner* — Jessica M Roswell
(74) *Attorney, Agent, or Firm* — Oblon, McClelland, Maier & Neustadt, L.L.P.

(57) ABSTRACT

The present invention relates to a diacrylate compound represented by general formula (1), a composition thereof, and a cured product of the compound/composition.

(1)

(Continued)

In the formula, R denotes a hydrogen atom or a methyl group; $R^1$, $R^2$, $R^3$, and $R^4$ each independently denote a $C_{1-6}$ linear or branched alkyl group, with the proviso that $R^1$, $R^2$, $R^3$, and $R^4$ are not all methyl groups.

The present invention provides: a novel diacrylate compound which can provide a cured product having an excellent balance of physical properties such as low curing shrinkage, flexibility, resistance to bending, and low curling properties, and which can be used as a photo- or thermal-radical polymerizable monomer; a composition of the compound; and a cured product of the compound/composition.

10 Claims, 3 Drawing Sheets

(51) Int. Cl.
| | |
|---|---|
| *C07C 67/03* | (2006.01) |
| *C07C 67/08* | (2006.01) |
| *C09D 4/02* | (2006.01) |
| *C07C 69/54* | (2006.01) |
| *C09D 11/101* | (2014.01) |
| *C08F 2/50* | (2006.01) |
| *C09J 4/02* | (2006.01) |
| *C08F 222/10* | (2006.01) |
| *C09D 4/00* | (2006.01) |
| *C09D 11/107* | (2014.01) |
| *C09J 4/00* | (2006.01) |
| *C09D 7/40* | (2018.01) |

(52) U.S. Cl.
CPC ............... *C07C 69/54* (2013.01); *C08F 2/50* (2013.01); *C08F 20/28* (2013.01); *C08F 220/28* (2013.01); *C09D 4/00* (2013.01); *C09D 7/40* (2018.01); *C09D 11/101* (2013.01); *C09D 11/107* (2013.01); *C09J 4/00* (2013.01); *C08F 2222/1013* (2013.01)

(58) Field of Classification Search
CPC ...... C09D 4/00; C09D 11/107; C09D 11/101; C09J 4/00; C07C 67/08; C07C 69/54; C07C 67/03

See application file for complete search history.

(56) References Cited

U.S. PATENT DOCUMENTS 5,217,760 A * 6/1993 Yang .................. C08F 2/50
427/517
2012/0203028 A1 8/2012 Beruben et al.

FOREIGN PATENT DOCUMENTS

| | | |
|---|---|---|
| JP | 10-204137 A | 8/1998 |
| JP | 2006-169374 A | 6/2006 |
| JP | 2010-209199 A | 9/2010 |
| JP | 2015-30677 A | 2/2015 |
| WO | 2014/104341 A1 | 7/2014 |

OTHER PUBLICATIONS

Kunihiro Ichimura, Chapter 5 Radical polymerizable monomer/oligomer. In UV-kouka no kiso to jissen (Fundamentals and Practice of UV-curing):, Yoneda Shuppan. pp. 55-69, (Oct. 7, 2010).

Eizo, Omori, "Shuju no Akuriru-san esuteru, kinousei akuriru-kei jushi (Various Acrylates. Functional Acrylic Resins)", Technosystem Co., Ltd., p. 159, (May 25, 1985).

International Search Report dated Sep. 8, 2015 in PCT/JP15/069207 Filed Jul. 2, 2015.

* cited by examiner

DIACRYLATE COMPOUND, COMPOSITION THEREOF, AND CURED PRODUCT THEREOF

TECHNICAL FIELD

The present invention relates to a novel diacrylate compound, a composition thereof, and a cured product of the compound/composition, and more specifically, relates to a diacrylate compound excellent in flexibility and low curling properties, a composition containing the compound, and a cured product of the compound/composition.

BACKGROUND ART

Photocurable resins, which cure through an ultraviolet ray or an electron beam, have short curing time and contain no solvents, and thus have advantages, such as resource saving performance, energy saving performance, and high productivity, over thermosetting resins. For this reason, photocurable resins are used for a variety of applications such as coating materials, coating agents, hard coating agents, inks, adhesives, pressure-sensitive adhesives, resists, molding materials, surface treatment agents, and surface modifiers. Acrylates and methacrylates are widely used for resin compositions containing such a photocurable resin because of the satisfactory curability (NPL 1).

In the resin composition, a diacrylate monomer or a dimethacrylate monomer is blended as a reactive diluent or a viscosity modifier. Examples of the diacrylate include 1,4-butanediol diacrylate, 1,6-hexanediol diacrylate, 1,9-nonanediol diacrylate, neopentyl glycol diacrylate, ethylene glycol diacrylate, polyethylene glycol diacrylate, dipropylene glycol diacrylate, and tripropylene glycol diacrylate. Examples of the dimethacrylate, in which the acrylate moiety of the diacrylate is replaced with methacrylate, include 1,4-butanediol dimethacrylate, 1,6-hexanediol dimethacrylate, 1,9-nonanediol dimethacrylate, neopentyl glycol dimethacrylate, ethylene glycol dimethacrylate, polyethylene glycol dimethacrylate, dipropylene glycol dimethacrylate, and tripropylene glycol dimethacrylate.

PTL 1 discloses that a coating agent the composition of which contains dineopentyl glycol diacrylate as a diluent at a content of 46% by mass based a polyester acrylate exhibits satisfactory adhesion and hardness.

However, neopentyl glycol diacrylate, 1,6-hexanediol diacrylate, neopentyl glycol dimethacrylate, 1,6-hexanediol dimethacrylate, and the like, which are commonly used, have high curing shrinkage, and thus have problems of lowering of flexibility and curling in curing. In addition, these diacrylates generally have a problem of high skin irritancy (NPL 1, NPL 2).

To reduce curing shrinkage and skin irritation, in many cases a diol as a raw material is modified into an alkylene oxide, and the modified product is converted into an acrylate for use. However, this method has a problem of lowering of curability concomitant with increase of viscosity by chain elongation (PTL). Moreover, use of such a modified product may lower the adhesiveness or the weatherability (NPL 1).

CITATION LIST

Patent Literature

PTL 1: JP 01-221348 A
PTL 2: JP 2010-209199 A

Non Patent Literature

NPL 1: Ichimura, Kunihiro, Chapter 5 Radical polymerizable monomer/oliger. In "UV-kouka no kiso to jissen (Fundamentals and Practice of UV-curing)", Yoneda Shuppan, Oct. 7, 2010, pp. 55-69
NPL 2: Omori, Eizo, "Shuju no Akuriru-san esuteru, kinousei akuriru-kei jushi (Various Acrylates, Functional Acrylic Resins)", Technosystem Co., Ltd., May 25, 1985, pp. 159

SUMMARY OF INVENTION

Technical Problem

Regarding the above problems, a compound as a diacrylate monomer or dimethacrylate monomer is required which has a good balance among low curing shrinkage, flexibility, low curling properties, resistance to bending, low skin irritancy, low molecular weight, low viscosity, satisfactory curability, etc.

PTL 1 describes only the hardness, curability, and adhesion of the coating agent, and does not disclose that the coating agent is satisfactory in physical properties such as flexibility, low curling properties, resistance to bending, and low curing shrinkage properties, and balance of physical properties.

On the basis of these circumstances, the present invention is intended to provide: a diacrylate compound having low curing shrinkage after curing and having an excellent balance of physical properties such as flexibility, resistance to bending, and low curling properties; a composition of the compound; and a cured product of the compound/composition.

Solution to Problem

As a result of various investigations to solve the above problems, the present inventors found novel diacrylate compounds. In addition, the present inventors found that the diacrylate compounds have low curing shrinkage and are excellent in resistance to bending and low curling properties, and thus completed the present invention. Specifically, the present invention is as follows.

[1] A diacrylate compound represented by the following general formula (1):

(1)

wherein R denotes a hydrogen atom or a methyl group; and $R^1$, $R^2$, $R^3$, and $R^4$ each independently denote a $C_{1-6}$ linear or branched alkyl group, with the proviso that $R^1$, $R^2$, $R^3$, and $R^4$ are not all methyl groups.

[2] The diacrylate compound according to [1], wherein, in the formula (1), combination of an alkyl group denoted as $R^1$ and an alkyl group denoted as $R^2$ is different from combination of an alkyl group denoted as $R^3$ and an alkyl group denoted as $R^4$.

[3] The diacrylate compound according to [1] or [2], wherein, in the formula (1), $R^1$ and $R^2$ are each a methyl group.

[4] A composition comprising: the diacrylate compound according to any one of [1] to [3]; and at least one selected from the group consisting of an additional polymerizable monomer, a polymerizable oligomer, and a radical polymerization initiator.

[5] The composition according to [4] comprising a radical polymerization initiator.

[6] The composition according to [4] comprising a photo-radical polymerization initiator.

[7] The composition according to any one of [4] to [6] comprising at least one selected from the group consisting of a urethane acrylate oligomer and a urethane methacrylate oligomer.

[8] A cured product obtained by curing the composition according to any one of [8] to [7].

[9] A cured product containing a structural unit represented by the following general formula (8):

$$\mathrm{-\!\!\left[\!CH_2\!-\!\underset{\underset{O}{\overset{\|}{C}}}{\overset{R}{\underset{|}{C}}}\!\right]\!\!-\!O\!-\!CH_2\!-\!\underset{R^2}{\overset{R^1}{\underset{|}{C}}}\!-\!CH_2\!-\!O\!-\!CH_2\!-\!\underset{R^4}{\overset{R^3}{\underset{|}{C}}}\!-\!CH_2\!-\!O\!-\!\underset{\underset{O}{\overset{\|}{C}}}{\overset{}{C}}\!-\!\!\left[\!CH_2\!-\!\overset{R}{\underset{|}{C}}\!\right]\!\!-} \quad (8)$$

wherein R denotes a hydrogen atom or a methyl group; and $R^1$, $R^2$, $R^3$, and $R^4$ each independently denote a $C_{1-6}$ linear or branched alkyl group, with the proviso that $R^1$, $R^2$, $R^3$, and $R^4$ are not all methyl groups.

[10] The cured product according to [9], wherein, in the formula (8), combination of an alkyl group denoted as $R^1$ and an alkyl group denoted as $R^2$ is different from combination of an alkyl group denoted as $R^3$ and an alkyl group denoted as $R^4$.

[11] An adhesive comprising the composition according to any one of [4] to [7].

[12] An ink comprising the composition according to any one of [4] to [7].

[13] A coating material comprising the composition according to any one of [4] to [7].

[14] A method for manufacturing a diacrylate compound, wherein a hindered polyol represented by the following general formula (2) and acrylic acid or methacrylic acid are allowed to undergo dehydration condensation reaction to afford a diacrylate compound represented by the following general formula (1):

$$\mathrm{HO}\!\!-\!\!\underset{\underset{}{}}{\overset{R^1\ R^2}{\diagup\!\!\diagdown}}\!\!-\!O\!-\!\underset{\underset{}{}}{\overset{R^3\ R^4}{\diagup\!\!\diagdown}}\!\!-\!\mathrm{OH} \quad (2)$$

$$\text{(1)}$$

wherein $R^1$, $R^2$, $R^3$, and $R^4$ each independently denote a $C_{1-6}$ linear or branched alkyl group, with the proviso that $R^1$, $R^2$, $R^3$, and $R^4$ are not all methyl groups; and R denotes a hydrogen atom or a methyl group.

[15] A method for manufacturing a diacrylate compound, wherein a hindered polyol represented by the following general formula (2) and an alkyl acrylate or alkyl methacrylate having a $C_{1-4}$ alkyl group are allowed to undergo transesterification reaction to afford a diacrylate compound represented by the following general formula (1):

$$\text{(2)}$$

$$\text{(1)}$$

wherein $R^1$, $R^2$, $R^3$, and $R^4$ each independently denote a $C_{1-6}$ linear or branched alkyl group, with the proviso that $R^1$, $R^2$, $R^3$, and $R^4$ are not all methyl groups and R denotes a hydrogen atom or a methyl group.

Advantageous Effects of Invention

The diacrylate compound according to the present invention can be used as a photo- or thermal-radical polymerizable monomer, and can provide a composition and a cured product which provide physical properties having an excellent balance among flexibility, resistance to bending, low curling properties, and low curing shrinkage.

DESCRIPTION OF EMBODIMENTS

Now, suitable embodiments of the present invention will be described in detail.

[Diacrylate Compound]

A diacrylate compound according to the present invention is represented by the following general formula (1). In the present specification, "diacrylate compound" encompasses compounds obtained by replacing the acrylate moiety of diacrylate compound with methacrylate.

(1)

In the formula (1), R denotes a hydrogen atom or a methyl group; and $R^1$, $R^2$, $R^3$, and $R^4$ each independently denote a $C_{1-6}$ linear or branched alkyl group, with the proviso that $R^1$, $R^2$, $R^3$, and $R^4$ are not all methyl groups. Examples of the alkyl group include a methyl group, an ethyl group, a n-propyl group, an isopropyl group, a n-butyl group, a sec-butyl group, an isobutyl group, a tert-butyl group, a n-pentyl group, and a n-hexyl group.

In the diacrylate compound represented by the formula (1), it is preferred that combination of an alkyl group denoted as $R^1$ and an alkyl group denoted as $R^2$ be different from combination of an alkyl group denoted as $R^3$ and an alkyl group denoted as $R^4$, it is more preferred that $R^1$ and $R^2$ be each a methyl group, and it is even more preferred that $R^1$ and $R^2$ be each a methyl group and $R^3$ and $R^4$ be a methyl group and a n-propyl group, respectively, or vice versa, or that $R^1$ and $R^2$ be each a methyl group and $R^3$ and $R^4$ be an ethyl group and a n-butyl group, respectively, or vice versa. Examples of the diacrylate compound having such combination include 2-((3-(acryloyloxy)-2,2-dimethylpropoxy)methyl)-2-ethylhexyl acrylate, 2-((3-(acryloyloxy)-2,2-dimethylpropoxy)methyl)-2-methylpentyl acrylate, 2-((3-(methacryloyloxy)-2,2-dimethylpropoxy)methyl)-2-ethylhexyl methacrylate, and 2-((3-methacryloyloxy)-2,2-dimethylpropoxy)methyl)-2-methylpentyl methacrylate.

A cured product obtained by polymerizing the diacrylate compound represented by the formula (1) according to the present invention exhibits physical properties having an excellent balance among resistance to bending, low curling properties, and low curing shrinkage. The reason is not clear, but is presumably as follows: the diacrylate compound represented by the formula (1) has steric hindrance due to the branched chain structure larger than those of diacrylate compounds having a linear chain structure such as 1,6-hexanediol diacrylate and 1,6-hexanediol dimethacrylate and those of diacrylate compounds having a short branched chain structure such as neopentyl glycol diacrylate and neopentyl glycol dimethacrylate, and has a flexible ether linkage; in addition, the diacrylate compound represented by the formula (1) has a longer branched chain structure than dineopentyl glycol diacrylate and dineopentyl glycol dimethacrylate; and thus the diacrylate compound represented by the formula (1) has lower curing shrinkage and more excellent physical properties such as, resistance to bending, and low curling properties than conventionally known diacrylate compounds.

[Method for Manufacturing Diacrylate Compound]

The diacrylate compound represented by the formula (1) is synthesized by allowing a hindered polyol represented by the following formula (2) and acrylic acid or methacrylic acid to undergo dehydration condensation reaction, or by allowing a hindered polyol represented by the following formula (2) and an alkyl acrylate or alkyl methacrylate to undergo transesterification reaction.

In the case of dehydration condensation reaction, the amount of acrylic acid or methacrylic acid to be used is preferably in the range of 2 to 10 mol, and more preferably 2 to 5 mol per mole of the polyol represented by the formula (2). In the case of transesterification reaction, the amount of an alkyl acrylate or alkyl methacrylate to be used is preferably in the range of 2 to 20 mol, and more preferably 2 to 8 mol per mole of the polyol represented by the formula (2).

(2)

In the formula (2) $R^1$, $R^2$, $R^3$, and $R^4$ are identical to those in the formula (1).

The hindered polyol represented by the formula (2) can be obtained through hydrogenation reduction of an acetal compound represented by general formula (3).

(3)

In the formula (3), $R^1$, $R^2$, $R^3$, and $R^4$ are identical to those in the formula (1).

The acetal compound represented by the general formula (3) can be obtained through acetalization of 2,2-disubstituted-3-hydroxypropanal and 2,2-disubstituted-1,3-propanediol.

(4)

In the formula (4), $R^1$, $R^2$, $R^3$, and $R^4$ are identical to those in the formula (1).

Dehydration condensation reaction of the polyol represented by the formula (2) and acrylic acid or methacrylic acid can be performed by using a known method with an acid catalyst, an organic solvent, and a polymerization inhibitor. The acid catalyst to be used for dehydration condensation reaction may be arbitrarily selected from known acid catalysts such as sulfuric acid, hydrochloric acid, phosphoric acid, methanesulfonic acid, p-toluenesulfonic acid, benzenesulfonic acid, boron trifluoride, and cationic ion-exchange resins.

One acid catalyst may be used singly, or two or more acid catalysts may be used in combination. The amount of the acid catalyst to be used is preferably 0.1 to 10% by mole, and more preferably 1 to 5% by mole relative to 1 mol of the polyol represented by the formula (2).

The organic solvent to be used for dehydration condensation reaction is not limited as long as the organic solvent does not cause a side reaction with any of the raw materials. To accelerate the reaction, an organic solvent which allows for distilling water to be generated away from the system, that is, a solvent which is separated from water to form two-layer structure and azeotropic with water can be used, and a solvent selected from the group consisting of hexane, heptane, cyclohexane, methylcyclohexane, benzene, toluene, and xylene can be suitably used.

One organic solvent may be used singly, or two or more organic solvents may be used in a mixture. The amount of the organic solvent to be used can be a minimum amount of the solvent required for azeotropic dehydration, which is calculated from the theoretical amount of water to be generated, and the azeotropic composition ratio between water and a kind of the solvent to be used. If a Dean-Stark apparatus is used, dehydration can be performed while an azeotropic solvent is continuously returned to a reaction vessel, and thus the amount of use can be smaller than the theoretical value. More simply, the amount of the organic solvent to be used is preferably 20 to 200% by mass, and more preferably 30 to 100% by mass based on the total mass of the polyol and acrylic acid or methacrylic acid to be used.

The polymerization inhibitor is not limited as long as the polymerization inhibitor can scavenge a radical, and may be arbitrarily selected from known polymerization inhibitors such as hydroquinone, p-methoxyphenol, t-butylhydroquinone, p-benzoquinone, and 2,2,6,6-tetramethylpiperidin-1-oxide. One polymerization initiator may be used singly, or two or more polymerization initiators may be used in combination.

The amount of the polymerization initiator for dehydration condensation reaction is preferably 0.001 to 5% by mass, and more preferably 0.01 to 1% by mass based on the amount of acrylic acid or methacrylic acid. The polymerization inhibitor may be optionally removed by washing with a basic aqueous solution after dehydration condensation reaction.

Transesterification reaction of the polyol represented by the formula (2) and an alkyl acrylate or alkyl methacrylate may be perfumed by using a known method with a polymerization inhibitor and at least one selected from the group consisting of a Lewis acid catalyst and a base catalyst.

The alkyl acrylate or alkyl methacrylate to be used for transesterification reaction may be a known alkyl acrylate or alkyl methacrylate having a $C_{1-4}$ alkyl group. Examples of the alkyl group include a methyl group, an ethyl group, a n-propyl group, an isopropyl group, and a n-butyl group. Among alkyl acrylates and alkyl methacrylates having a $C_{1-4}$ alkyl group, methyl acrylate and methyl methacrylate are preferred because use of them facilitates distillation of an alcohol to be generated.

Moreover, it is suitable to perform the reaction while a lower alcohol is distilled away with use of a reactor provided with a distillation column because removal of a lower alcohol to be generated in the reaction from the reaction system allows the reaction to proceed quickly.

Examples of the Lewis acid catalyst to be used for transesterification reaction include dimethyltin oxide, dibutyltin oxide, dimethyltin dichloride, dibutyltin dichloride, aluminum isopropoxide, zinc acetylacetonate, tetramethoxytitanium, tetraisopropoxytitanium, and tetrabutoxytitanium. Alternatively, any of the Lewis acid catalysts may be generated in the reaction system by using a base.

Examples of the base catalyst to be used for transesterification reaction include lithium methoxide, sodium methoxide, potassium methoxide, lithium ethoxide, sodium ethoxide, and potassium ethoxide.

One catalyst may be used singly, or two or more catalysts may be appropriately used in combination as long as no problem arises.

The amount of the polymerization inhibitor to be used for transesterification reaction is preferably 0.001 to 3% by mass, and more preferably 0.005 to 1% by mass based on the amount of the alkyl acrylate or alkyl methacrylate. The polymerization inhibitor may be optionally removed by washing with a basic aqueous solution after transesterification reaction.

For example, the diacrylate compound according to the present invention can be used as a reactive diluent or a viscosity modifier for applications such as coating materials, coating agents, hard coating agents, inks, adhesives, pressure-sensitive adhesives, resists, molding materials, and surface treatment agents.

Further, 2-((3-(acryloyloxy)-2,2-dimethylpropoxy)methyl)-2-ethylhexyl acrylate (NBDA), a diacrylate compound according to the present invention, has been found to have a primary skin irritation index of mild irritation.

[Composition]

A composition according to the present invention contains the diacrylate compound represented by the formula (1) and at least one selected from the group consisting of an additional polymerizable monomer, a polymerizable oligomer, and a radical polymerization initiator.

When the diacrylate compound according to the present invention is polymerized to obtain a cured product, the diacrylate compound may be homopolymerized or may be copolymerized with an additional polymerizable monomonomer or a polymerizable oligomer in accordance with the application. An additional polymerizable monomer or polymerizable oligomer to be copolymerized may be used singly, or two or more additional polymerizable monomers or polymerizable oligomers may be used in combination.

The polymerizable monomer or polymerizable oligomer to be copolymerized is not limited, and examples of the polymerizable monomer include acrylic monomers having an acryloyl group, methacrylic monomers having a methacryloyl group, and styrene derivatives. Examples of the acrylic monomer include methyl acrylate, ethyl acrylate, n-butyl acrylate, n-hexyl acrylate, 2-ethylhexyl acrylate, lauryl acrylate, dicyclopentenyl acrylate, dicyclopentanyl acrylate, isobornyl acrylate, tetrafurfuryl acrylate, phenoxyethyl acrylate, 2-hydroxyethyl acrylate, polypropylene glycol diacrylate, trimethylolpropane triacrylate, pentaerythritol tetraacrylate, ditrimethylolpropane tetraacrylate, and dipentaerythritol hexaacrylate.

Examples of the methacrylic monomer include methyl methacrylate, ethyl methacrylate, n-butyl methacrylate, n-hexyl methacrylate, 2-ethylhexyl methacrylate, lauryl methacrylate, dicyclopentenyl methacrylate, dicyclopentanyl methacrylate, isobornyl methacrylate, tetrafurfuryl methacrylate, phenoxyethyl methacrylate, 2-hydroxyethyl methacrylate, polypropylene glycol dimethacrylate, trimethylolpropane trimethacrylate, pentaerythritol tetramethacrylate, ditrimethylolpropane tetramethacrylate, and dipentaerythritol hexamethacrylate.

Examples of the polymerizable oligomer include polyester acrylate oligomers, epoxy acrylate oligomers, urethane acrylate oligomers, polyester methacrylate oligomers, epoxy methacrylate oligomers, and urethane methacrylate oligomers.

Among them, at least one selected from the group consisting of a urethane acrylate oligomer and a urethane methacrylate oligomer is preferred from the viewpoint of excellent mechanical properties and UV curability.

Although the urethane acrylate oligomer and urethane methacrylate oligomer to be used in the present invention are not limited, urethane acrylate oligomers obtained from a polyol, a polyisocyanate, and a hydroxy group-containing acrylate, and urethane methacrylate oligomers obtained from a polyol, a polyisocyanate, and a hydroxy group-containing methacrylate are preferred, and urethane acrylate oligomers having one acryloyl group at each end (bifunctional urethane acrylate oligomers) and urethane methacrylate oligomers having one methacryloyl group at each end (bifunctional urethane methacrylate oligomers) are more preferred. Examples thereof include compounds represented by the following general formula (7).

(7)

In the formula (7), $R^5$ denotes a residue of a hydroxy group-containing acrylate or hydroxy group-containing methacrylate; $R^6$ denotes a residue of a polyisocyanate; $R^7$ denotes a residue of a polyol; and m is an integer of 1 to 20. A plurality of each of $R^5$, $R^6$, and $R^7$ may be identical or different.

"Residue" in the above refers to a residual portion obtained by removing functional groups each forming a urethane linkage from the material structure of the urethane acrylate oligomer and urethane methacrylate oligomer represented by the formula (7), and specifically, refers to a residual portion obtained by removing hydroxyl groups in the case of a hydroxy group-containing acrylate or hydroxy group-containing methacrylate (denoted as $R^5$), a residual portion obtained by removing isocyanate groups in the case of a polyisocyanate (denoted as $R^6$), and a residual portion obtained by removing hydroxyl groups in the case of a polyol (denoted as $R^7$).

To obtain the urethane acrylate oligomer and urethane methacrylate oligomer, a conventionally known method may be used without any limitation. Example of the method include a method in which a polyol and a polyisocyanate are reacted under a condition of excessive isocyanate groups (under a condition of 1 or more mole equivalents of polyisocyanate per mole equivalent of a polyol used as a raw material), and then at least one selected from the group consisting of a hydroxy group-containing acrylate and a hydroxy group-containing methacrylate is further reacted therewith.

Examples of the hydroxy group-containing acrylate include 2-hydroxyethyl acrylate, 2-hydroxypropyl acrylate, 2-hydroxybutyl acrylate, 4-hydroxybutyl acrylate, 2-hydroxy-3-phenoxypropyl acrylate, glycerin diacrylate, trimethylolpropane diacrylate, pentaerythritol triacrylate, and dipentaerythritol pentaacrylate.

Examples of the hydroxy group-containing methacrylate include 2-hydroxyethyl methacrylate, 2-hydroxypropyl methacrylate, 2-hydroxybutyl methacrylate, 4-hydroxybutyl methacrylate, 2-hydroxy-3-phenoxypropyl methacrylate, glycerin dimethacrylate, trimethylolpropane dimethacrylate, pentaerythritol trimethacrylate, and dipentaerythritol pentamethacrylate.

One hydroxy group-containing acrylate or hydroxy group-containing methacrylate may be used singly, or two or more hydroxy group-containing acrylates or hydroxy group-containing methacrylates may be used in combination. Alternatively, the hydroxy group-containing acrylate and the hydroxy group-containing methacrylate may be used in combination.

Examples of the polyisocyanate include aliphatic diisocyanates such as methylene diisocyanate, propylene diisocyanate, lysine diisocyanate, trimethylhexamethylene diisocyanate, and hexamethylene diisocyanate; alicyclic diisocyanates such as cyclohexane diisocyanate, methylcyclohexane diisocyanate, isophorone diisocyanate, dicyclohexylmethane diisocyanate, and isopropylidenedicyclohexyl diisocyanate; aliphatic diisocyanates having an aromatic ring such as α,α,α',α'-tetramethyxylylene diisocyanate; and aromatic diisocyanates such as tolylene diisocyanate, xylylene diisocyanate, methylenediphenyl diisocyanate, phenylene diisocyanate, naphthalene diisocyanate, and tolidine diisocyanate. Among them, aliphatic diisocyanates and alicyclic diisocyanates are preferred from the viewpoint of no yellowing. One polyisocyanate may be used singly, or two or more polyisocyanates may be used in combination.

For the polyol, an aromatic, aliphatic, or alicyclic polyol is typically used, and a polyester polyol, a polyether polyol, a polycarbonate polyol, or the like is also used.

Examples of the aliphatic and alicyclic polyols include aliphatic diols such as ethylene glycol, propylene glycol, trimethylene glycol, 1,4-butylene glycol, 1,3-butylene glycol, 1,2-butylene glycol, 1,5-pentanediol, 3-methyl-1,5-pentanediol, 2,2-dimethyl-1,3-propanediol, 1,6-hexanediol, 2,2-diethyl-1,3-propanediol, 3,3-dimethylolheptane, 2-ethyl-2-butyl-1,3-propanediol, 1,12-dodecanediol, and 1,18-octadecanediol; alicyclic diols such as 1,4-cyclohexanediol, 1,4-cyclohexanedimethanol, and hydrogenated bisphenol A; aliphatic triols such as glycerin, 2-methyl-2-hydroxymethyl-1,3-propanediol, 2,4-dihydroxy-3-hydroxymethylpentane, 1,2,6-hexanetriol, trimethylolethane, trimethylolpropane, 2-methyl-2-hydroxymethyl-1,3-propanediol, 2,4-dihydroxy-3-(hydroxymethyl)pentane, and 2,2-bis(hydroxymethyl)-3-butanol; and polyols having four or more hydroxy groups such as tetramethylolmethane, pentaerythritol, dipentaerythritol, and xylitol. Among polyols, aliphatic polyols and alicyclic polyols are preferred from the viewpoint lowering the viscosity of an oligomer.

A polyester polyol is obtained by allowing any of the above compounds and a polybasic carboxylic acid or an anhydride thereof to undergo dehydration condensation reaction. Specific examples of the polybasic carboxylic acid compound include succinic acid, succinic anhydride, adipic acid, maleic acid, maleic anhydride, trimellitic acid, trimellitic anhydride, phthalic acid, phthalic anhydride, isophthalic acid, and terephthalic acid.

Examples of the polyether polyol include polyalkylene glycols such as polyethylene glycol, polypropylene glycol, polytetramethylene glycol, and polyheptamethylene glycol; and polyoxyalkylene-modified polyols obtained by reacting any of the above polyols or a phenol with an alkylene oxide.

Examples of the polycarbonate polyol include compounds obtained by reacting any of the above polyols with a carbonate compound such as a dialkyl carbonate, an alkylene carbonate, and diphenyl carbonate.

Among them, at least one selected from the group consisting of a polyester polyol and a polyether polyol is preferred, and a polyether polyol is more preferred from the viewpoint of flexibility, adhesion, etc. One polyol may be used singly, or two or more polyols may be used in combination.

In the case, that a cured product is obtained as a copolymer, the amount of the diacrylate compound represented by the formula (1) to be blended in the composition according to the present invention is preferably 20 to 90% by mass, more preferably 30 to 80% by mass, and even more preferably 40 to 70% by mass based on the total mass of the diacrylate compound according to the present invention, the additional polymerizable monomer, and the polymerizable oligomer, from the viewpoint of providing physical properties having an excellent balance among flexibility, resistance to bending, low curling properties, and low curing shrinkage. Similarly, the total amount of the additional polymerizable monomer and the polymerizable oligomer is preferably 10 to 80% by mass, more preferably 20 to 70% by mass, and even more preferably 30 to 60% by mass based on the total mass of the diacrylate compound according to the present invention, the additional polymerizable monomer, and the polymerizable oligomer.

The composition according to the present invention preferably contains a radical polymerization initiator.

The radical polymerization initiator is not limited as long as it is commonly used as a polymerization initiator, and a photo-radical polymerization initiator and a thermal-radical initiator can be used, and it is preferred to use photo-radical polymerization initiator. Examples of the photo-radical polymerization initiator include acetophenone, p-anisil, benzoin, benzoin methyl ether, benzoin isobutyl ether, dibenzoyl, and 1-hydroxycyclohexyl phenyl ketone. Examples of the thermal-radical polymerization initiator include 2,2'-azobis(isobutyronitrile), 2,2'-azobis(2,4-dimethylvaleronitrile), and benzoyl peroxide. One radical polymerization initiator may be used singly, or two or more radical polymerization initiators may be used in combination.

The amount of the radical polymerization initiator to be blended in the composition is preferably 0.1 to 10 parts by mass, more preferably 1 to 8 parts by mass, and even more preferably 2 to 6% by mass based on 100 parts by mass of the total amount of the diacrylate compound according to the present invention, the additional polymerizable monomer, and the polymerizable oligomer.

For the above composition, various additives may be used, as necessary, to provide desired physical properties. Examples of the additive include pigments, dyes, defoamers, anti-sagging agents, adhesion enhancers, plasticizers, dispersants, surface smoothers, viscosity modifiers, antistatic agents, mold release agents, light-diffusing agent, and antioxidants. In addition, an inorganic filler such as a glass fiber, a carbon fiber, and a clay compound may be added to the above composition. One of these additives may be used singly, or two or more thereof may be used in combination.

Although the above composition may be used with no solvents, an organic solvent may be blended therein in accordance with a base material to be used, an application method, etc. The organic solvent is not limited, and examples thereof include hexane, heptane, toluene, xylene, methanol, ethanol, diethyl ether, tetrahydrofuran, 1,4-dioxane, ethyl acetate, acetone, methyl ethyl ketone, and cyclohexanone. One organic solvent may be used singly, or two or more organic solvents may be used in combination.

[Cured Product]

A cured product according to the present invention is obtained by curing the above composition. Examples of the method for obtaining the cured product according to the present invention include a method in which, to the diacrylate compound represented by the formula (1), one or more selected from the group consisting of an additional polymerizable monomer, a polymerizable oligomer, and a radical polymerization initiator are added to prepare a composition, and the composition is subjected to photo- or thermal-radical polymerization.

The cured product according to the present invention may be a homopolymer of the diacrylate compound represented by the formula (1), or may be a copolymer of the diacrylate compound represented by the formula (1) with at least one selected from the group consisting of an additional polymerizable monomer and a polymerizable oligomer. Among them, a copolymer containing a structural unit derived from the diacrylate compound represented by the formula (1) and a structural unit derived from at least one selected from the group consisting of a urethane acrylate oligomer and a urethane methacrylate oligomer is preferred from the viewpoint of providing physical properties having an excellent balance among flexibility, resistance to bending, low curling properties, and low curing shrinkage.

The cured product according to the present invention contains a structural unit represented by the following general formula (8). The structural unit represented by the formula (8) is a structural unit derived from the diacrylate compound represented by the formula (1).

In the formula (8), R denotes a hydrogen atom or a methyl group; and $R^1$, $R^2$, $R^3$, and $R^4$ each independently denote a $C_{1-6}$ linear or branched alkyl group, with the proviso that $R^1$, $R^2$, $R^3$, and $R^4$ are not all methyl groups. The alkyl group has the same definition as described for the formula (1).

In the formula (8), it is preferred that combination of an alkyl group denoted as $R^1$ and an alkyl group denoted as $R^2$ be different from combination of an alkyl group denoted as $R^3$ and an alkyl group denoted as $R^4$, it is more preferred that $R^1$ and $R^2$ be each a methyl group, and it is even more preferred that $R^1$ and $R^2$ be each a methyl group and $R^3$ and $R^4$ be a methyl group and a n-propyl group, respectively, or vice versa, or that $R^1$ and $R^2$ be each a methyl group and $R^3$ and $R^4$ be an ethyl group and a n-butyl group, respectively, or vice versa.

In the case that the cured product according to the present invention is the above copolymer, the cured product preferably contains the structural unit represented by the above general formula (8) and a structural unit represented by the following general formula (9). The structural unit represented by the formula (9) is a structural unit derived from at least one selected from the group consisting of a urethane acrylate oligomer and a urethane methacrylate oligomer.

(9)

In the formula (9), $R^6$ denotes a group obtained by removing isocyanate groups each forming a urethane linkage from the structure of a polyisocyanate, a material of at least one selected from the group consisting of a urethane acrylate oligomer and a urethane triethacrylate oligomer; $R^7$ denotes a group obtained by removing hydroxyl groups each forming a urethane linkage from the structure of a polyol, a material of at least one selected from the group consisting of a urethane acrylate oligomer and a urethane methacrylate oligomer; $R^8$ denotes a group obtained by removing acryloyl groups and hydroxyl groups each forming a urethane linkage from the structure of a hydroxy group-containing acrylate, a material of a urethane acrylate oligomer, or denotes a group obtained by removing methacryloyl groups and hydroxyl groups each forming a urethane linkage from the structure of a hydroxy group-containing methacrylate, a material of a urethane methacrylate oligomer; $R^9$ denotes a hydrogen atom or a methyl group; and m is an integer of 1 to 20. A plurality of each of $R^6$, $R^7$, $R^8$, and $R^9$ may be identical or different.

The cured product according to the present invention can be obtained by irradiating the above composition with an active energy ray and/or by heating the above composition. Examples of the active energy ray include infrared rays, visible rays, ultraviolet rays, X-rays, electron beams, α-rays, β-rays, and γ-rays. It is preferred to use an electron beam or a ultraviolet ray from the viewpoint of apparatus cost and productivity, and examples of the suitable light source include an electron beam irradiator, an ultrahigh-pressure mercury lamp, a high-pressure mercury lamp, a middle-pressure mercury lamp, a low-pressure mercury lamp, a metal halide lamp, an Ar laser, a He—Cd laser, a solid laser, a xenon lamp, a high-frequency induction mercury lamp, and solar light.

The amount of irradiation with an active energy ray can be appropriately selected in accordance with the type of an active energy ray. In the case that irradiation with an electron beam is used for curing, for example, the amount of irradiation is preferably 1 to 15 Mrad. In the case that irradiation with an ultraviolet ray is used for curing, the amount of irradiation is preferably 50 to 2000 mJ/cm².

In the case that heating is used for curing, the curing temperature is preferably 30 to 150° C., more preferably 40 to 120° C., and even more preferably 50 to 100° C.

Although curing may be performed under any atmosphere of air or an inert gas, such as nitrogen, and argon, it is desirable to irradiate in an inert gas or in an enclosed space between a film or a glass and a metal mold to prevent oxygen interference.

Although the thickness of the cured product according to the present invention can be appropriately set in accordance with an intended application, the thickness is preferably 1 to 100 μm, and more preferably 3 to 70 μm.

The cured product according to the present invention is preferably obtained by application of the above composition onto a base material followed by curing. Examples of the base material include articles of various forms, such as a sheet, etc., made of a plastic examples of which include polyesters such as polyethylene terephthalate and polybutylene terephthalate, polyolefins such as polypropylene, and polyethylene, nylons, polycarbonates, acrylic resins, and methacrylic resins, glass, or a metal.

The application method is not limited, and a conventionally known method may be used such as a die coater, a comma coater, a curtain coater, a gravure coater, a roll coater, a spray coater, a spin coater, and inkjet.

EXAMPLES

Now, the present invention will be described in more detail with reference to Examples, but the present invention is not limited to the following Examples.

Reaction analysis was performed by using gas chromatography. For gas chromatography, a 7890A manufactured by Agilent Technologies Inc. was used. For the column, a DB-1701 manufactured by Agilent J&W was used. Regarding the column temperature and the temperature elevation rate, the temperature was retained at 40° C. for 5 minutes, and then elevated to 250° C. at 10° C./min, and then retained for 15 minutes. The injection temperature was 210° C., and a TCD was used for the detector at 250° C. For the carrier gas, helium was used.

Identification of a product was performed by using $^1$H NMR spectrum and $^{13}$NMR spectrum at a frequency of 500 MHz and 125 MHz, respectively. For the measurement solvent, CDCl$_3$ was used. For the measurement apparatus, a JNM-ECA500 manufactured by JEOL Ltd. was used.

Synthesis Example 1

Synthesis of 2-(5-butyl-5-ethyl-1,3-dioxan-2-yl)-2-methylpropan-1-ol

In a 2 L round-bottom flask, 73.6 g of 2,2-dimethyl-3-hydroxypropanal, 111.8 g of 2-butyl-2-ethyl-1,3-propanediol, 705 g of benzene, and 3.0 g of a particulate Nafion (product name: "NR-50", manufactured by Sigma-Aldrich Co.) were contained, and allowed to react while water generated was azeotroped with the benzene under normal pressure to remove from the system by using a Dean-Stark apparatus until distillation of water was ceased. The reaction product was filtered and concentrated, and then subjected to distillation under reduced pressure to afford the intended product at a % yield of 99%. The reaction formula of the reaction is shown in formula (5)

(5)

A catalyst for hydrogenation of an acetal was synthesized as follows.

Preparation of Carrier

Zirconium oxide used for a carrier for a metal component was prepared in accordance with the following method.

To 505 g of an aqueous solution of zirconium oxynitrate having a concentration of 25% by mass in terms of zirconium oxide ($ZrO_2$), 15.5 g of 28% ammonia water was added dropwise under stirring to afford a white precipitate. This precipitate was filtered out and washed with ion-exchanged water, and then dried at 110° C. for 10 hours to afford hydrous zirconium oxide. This was contained in a porcelain crucible and calcined in the air at 400° C. for 3 hours by using an electric furnace. Thereafter, the resultant was pulverized with an agate mortar to afford a powder zirconium oxide (hereinafter, referred to as "carrier A"). The BET specific surface area (measured by using a nitrogen adsorption method) of the carrier A was 102.7 $m^2$/g.

Preparation of Catalyst

A catalyst containing palladium as a specific metal component was prepared in accordance with the following method.

An aqueous solution of 0.66% by mass palladium chloride-0.44% by mass sodium chloride was added to 50 g of the carrier A to allow the carrier to adsorb the metal component thereon. Thereto, an aqueous solution of formaldehyde-sodium hydroxide was pouted to reduce the adsorbed metal component instantaneously. The catalyst was then washed with ion-exchanged water, and dried to prepare a 1.0% by mass palladium-supporting zirconium oxide catalyst (hereinafter, referred to as "catalyst A").

Synthesis Example 2

Synthesis of 2-ethyl-2-(3-hydroxy-2,2-dimethyl-propoxymethyl)-hexan-1-ol

In a 500 mL SUS reactor, 3.0 g of the catalyst A, 60.0 g of 2-(5-butyl-5-ethyl-1,3-dioxan-2-yl)-2-methylpropan-1-ol obtained in Synthesis Example 1, and 240 g of 1,4-dioxane were contained, and the inside of the reactor was purged with nitrogen gas. Thereafter, the inside of the reactor was filled with hydrogen gas to a pressure of 8.5 MPa, and the temperature was elevated to the reaction temperature of 230° C. to adjust the pressure to 13 MPa. A reaction was performed at 230° C. for 5 hours while the reactor was filled with hydrogen so that the reaction pressure was retained at 13 MPa. Thereafter, the reactor was cooled and the content of the reactor was filtered to separate the catalyst, and then subjected to distillation purification under reduced pressure to afford the intended product. The reaction formula of the reaction is shown in formula (6).

(6)

Example 1

Synthesis of 2-((3-(acryloyloxy)-2,2-dimethyl-propoxy)methyl)-2-ethylhexyl acrylate (NBDA)

In a glass reactor provided with a stirrer, a thermometer, and a Vigreux column, 2-ethyl-2-(3-hydroxy-2,2-dimethyl-propoxymethyl)-hexan-1-ol (30.0 g, 122 mmol), methyl acrylate (42.2 g, 487 mmol), dimethyltin dichloride (268 mg, 1.2 mmol), sodium methoxide (67 mg, 1.2 mmol), p-methoxyphenol (91 mg, 0.7 mmol), and hydroquinone (39 mg, 0.4 mmol) were mixed together. The mixture was warmed at an internal temperature of 85 to 105° C. and stirred under heating for 31 hours while methanol was distilled away from the system through azeotroping with methyl acrylate. The catalyst and the polymerization inhibitor were removed by washing with a basic aqueous solution, and unreacted methyl acrylate was then distilled away under reduced pressure to afford the intended product (yield: 37.3 g, purity: 94.0%, 99 mmol, % yield: 81%).

(Compound NBDA)

Figure 1:
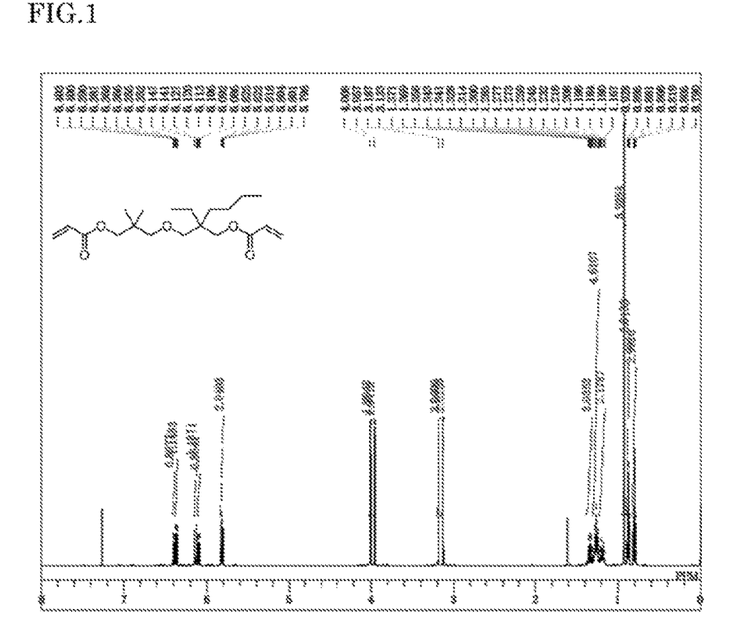
FIG. 1 is a $^1$H-NMR chart of 2-((3-(acryloyloxy)-2,2-dimethylpropoxy)methyl)-2-ethylhexyl acrylate NBDA), a diacrylate compound obtained in Example 1.
Figure 2:
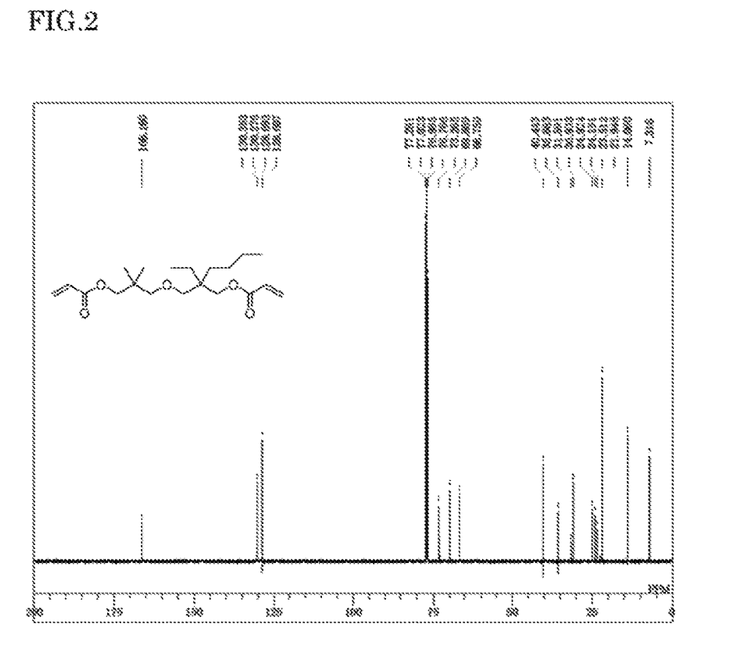
FIG. 2 is a $^{13}$C-NMR chart of NBDA, a diacrylate compound obtained in Example 1.

The product obtained in Example 1 was identified through the $^1$H NMR spectrum and the $^{13}$C NMR spectrum to be a novel compound represented by the following chemical structural formula. In the present specification, the compound is occasionally referred to as NBDA.

NBDA: oily, colorless.

$^1$H NMR δ 0.80 (t, —C$\underline{H}_3$, 3H), 0.88 (t, —C$\underline{H}_3$, 3H), 0.93 (s, —C(C$\underline{H}_3$)$_2$, 6H), 1.17-1.36 (m, —(C$\underline{H}_2$)$_3$CH$_3$ & —C$\underline{H}_2$CH$_3$, 8H), 3.13 (s, —C$\underline{H}_2$O—, 2H), 3.19 (s, —C$\underline{H}_2$O—, 2H), 3.96 (s, —COOC$\underline{H}_2$—, 2H), 4.01 (s, —COOC$\underline{H}_2$, 2H), 5.81 (dd, $\underline{H}_a$', 1H), 5.81 (dd, $\underline{H}_a$, 1H), 6.11 (dd, $\underline{H}_b$', 1H), 6.12 (dd, $\underline{H}_b$, 1H), 6.37 (dd, $\underline{H}_c$', 1H), 6.38 (dd, $\underline{H}_c$, 1H).

$^{13}$C NMR δ. 7.32, 14.06, 21.95, 23.51, 24.15, 24.92, 30.93, 31.59, 35.68, 40.45, 66.75, 69.87, 73.26, 76.99, 128.61, 128.69, 130.28, 130.35, 166.16 (×2C).

Primary skin irritation index (P.I.I.): In accordance with OECD Test Guideline No. 404 (2002), NBDA synthesized in Example 1 was subjected to a primary skin irritation test. The P.I.I. of NBDA was 1.3. This P.I.I. was smaller than those of neopentyl glycol diacrylate (P.I.I.=4.96) and 1,6-hexanediol diacrylate=5.0), which are commonly used, and was classified as mild irritation.

Example 2

Synthesis of 2-((3-acryloyloxy)-2,2-dimethyl-propoxy)methyl)-2-methylpentyl acrylate (NMDA)

In a glass reactor provided with a stirrer, a thermometer, and a Vigreux column, 2-(3-hydroxy-2,2-dimethyl-propoxymethyl)-2-methyl-pentan-1-ol (38.0 g, 174 mmol), methyl acrylate (63.9 g, 732 mmol, dimethyltin dichloride (1.2 g, 5.5 mmol), sodium methoxide (300 mg, 0.55 mmol), and p-methoxyphenol (189 mg, 1.5 mmol) were mixed together. The mixture was warmed at an internal temperature of 85 to 105° C. and stirred under heating for 20 hours while methanol was distilled away from the system through azeotroping with methyl acrylate. The catalyst and the polymerization inhibitor were removed by washing with a basic aqueous solution, and unreacted methyl acrylate was then distilled away under reduced pressure to afford the intended product (yield: 51.5 g, purity: 96.5%, 152 mmol, % yield: 87%).

(Compound NMDA)

Figure 3:
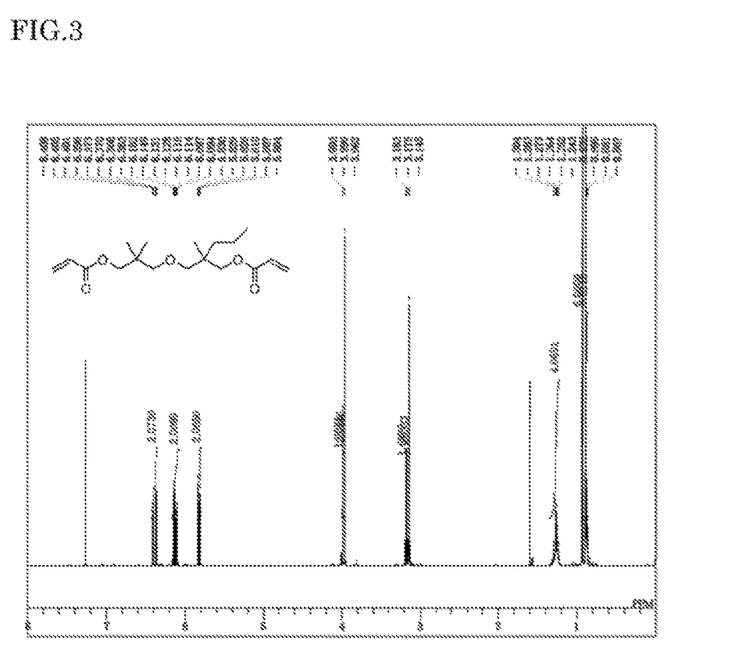
FIG. 3 is a $^1$H-NMR chart of 2-((3-(acryloyloxy)-2,2-dimethylpropoxy)methyl)-2-methylpentyl acrylate (NMDA), a diacrylate compound obtained in Example 2.
Figure 4:
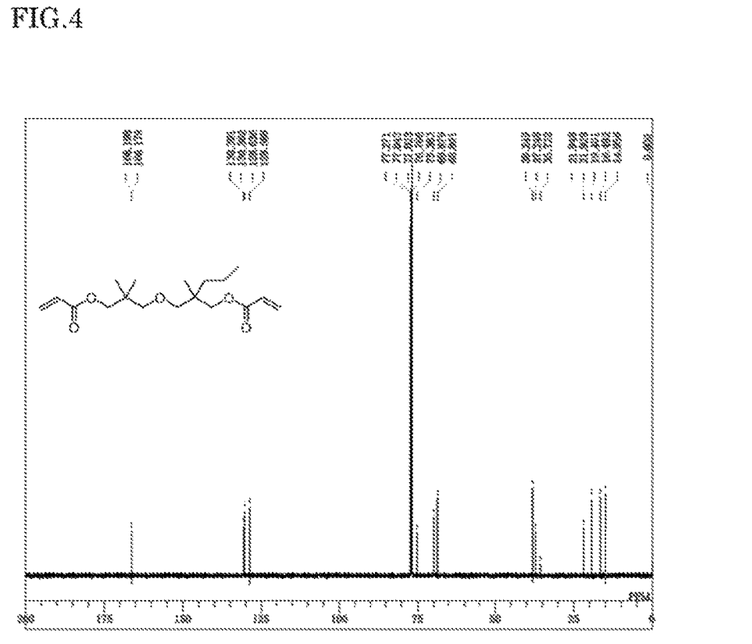
FIG. 4 is a $^{13}$C-NMR chart of NMDA, a diacrylate compound obtained in Example 2

The product obtained in Example 2 was identified through the $^1$H NMR spectrum and the $^{13}$C NMR spectrum to be a novel compound represented by the following chemical structural formula. In the present specification, the compound is occasionally referred to as NMDA.

NMDA: oily, colorless.

$^1$H NMR δ 0.87-0.90 (m, —C$\underline{H}_3$ & —(CH$_2$)$_2$C$\underline{H}_3$, 6H), 0.93 (s, —C(C$\underline{H}_3$)$_2$, 6H), 1.24-1.30 (m, —(C$\underline{H}_2$)$_2$CH$_3$, 4H), 3.14 (s, —C$\underline{H}_2$O—, 2H), 3.18 (d, —C$\underline{H}_2$O—, 2H), 3.96 (s, —COOC$\underline{H}_2$—, 2H), 3.99 (d, —COOC$\underline{H}_2$, 2H), 5.82 (dd, H$_a$', 1H), 5.82 (dd, H$_a$, 1H), 6.11 (dd, H$_b$', 1H), 6.13 (dd, H$_b$, 1H), 6.38 (dd, H$_c$', 1H), 6.39 (dd, H$_c$, 1H).

$^{13}$C NMR δ 14.96, 16.49, 19.40, 21.93, 21.95, 35.72, 37.25, 38.25, 68.80, 69.88, 75.36, 77.04, 128.59, 128.64, 130.36, 130.39, 166.18, 166.20.

Example 3

Synthesis of 2-((3-(methacryloyloxy)-2,2-dimethyl-propoxy)methyl)-2-ethylhexyl methacrylate (NBDM)

In a glass reactor provided with a stirrer, thermometer, and a Vigreux column, 2-ethyl-2-(3-hydroxy-2,2-dimethyl-propoxymethyl)-hexan-1-ol (20.0 g, 81 mmol), methyl methacrylate (32.7 g, 324 mmol), dimethyltin dichloride (533 mg, 2.4 mmol), sodium methoxide (134 mg, 2.4 mmol), p-methoxyphenol (66 mg, 0.5 mmol), and hydroquinone (28 mg, 0.3 mmol) were mixed together. The mixture was warmed at an internal temperature of 100 to 115° C. and stirred under heating for 24 hours while methanol was distilled away from the system through azeotroping with methyl methacrylate. The catalyst and the polymerization inhibitor were removed by washing with a basic aqueous solution, and unreacted methyl methacrylate was then distilled away under reduced pressure to afford the intended product (yield: 29.6 g, purity: 93.6%, 72 mmol, % yield: 89%).

(Compound NBDM)

Figure 5:
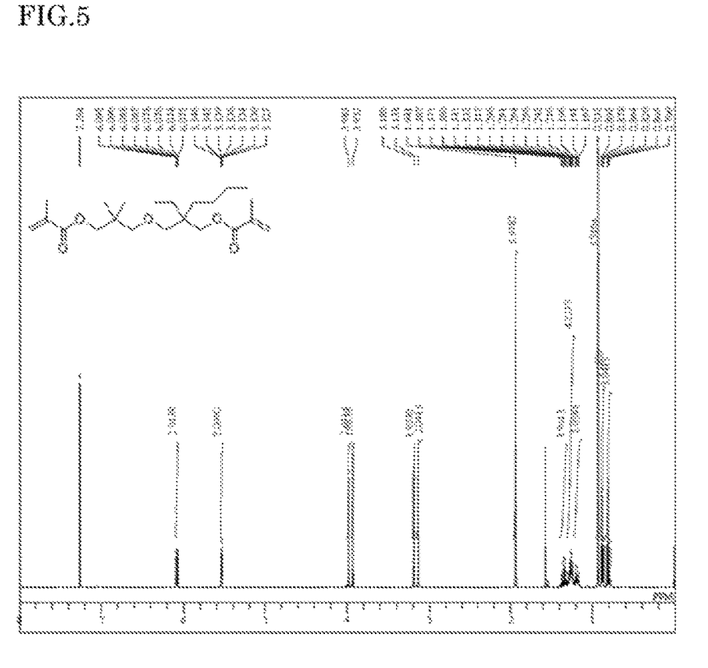
FIG. 5 is a $^1$H-NMR chart of 2-((3-(methacryloyloxy)-2,2-dimethylpropoxy)methyl)-2-ethylhexyl methacrylate (NBDM), a diacrylate compound obtained in Example 3.
Figure 6:
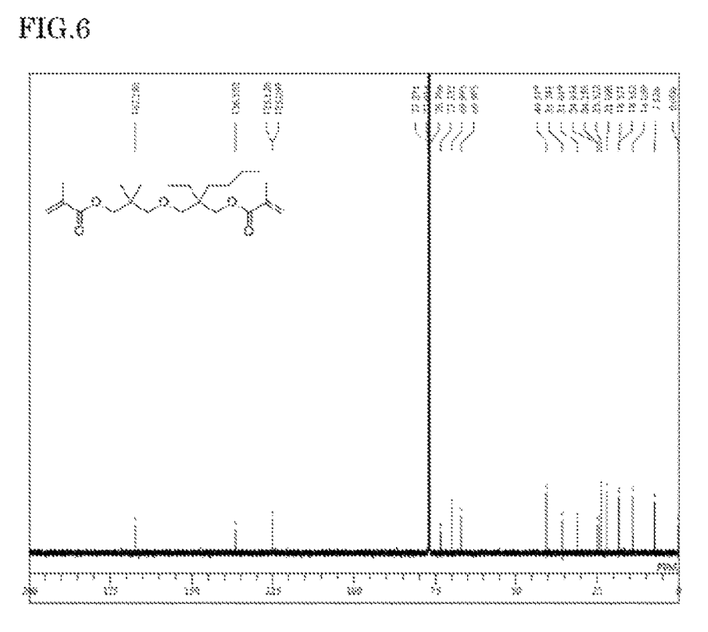
FIG. 6 is a $^{13}$C-NMR chart of NBDM, a diacrylate compound obtained in Example 3.

The product obtained in Example 3 was identified through the $^1$H NMR spectrum and the $^{13}$C NMR spectrum to be a novel compound represented by the following chemical structural formula. In the present specification, the compound is occasionally referred to as NBDM.

NBDM: oily, colorless.

$^1$H NMR δ 0.81 (t, —C$\underline{H}_3$, 3H), 0.88 (t, —C$\underline{H}_3$, 3H), 0.93 (s, —C(C$\underline{H}_3$)$_2$, 6H) 1.17-1.39 (m, —(C$\underline{H}_2$)$_3$CH$_3$ & —C$\underline{H}_2$CH$_3$, 8H), 1.94 (s, C(CH$_3$)$_2$, 6H), 3.14 (s, —C$\underline{H}_2$O—, 2H), 3.19 (s, —C$\underline{H}_2$O—, 2H), 3.93 (s, —COOC$\underline{H}_2$—, 2H), 3.98 (s, —COOC$\underline{H}_2$, 2H), 5.52-5.55 (m, H$_a$ & H$_a$' 2H), 6.07-6.09 (m, H$_b$ & H$_b$', 2H).

$^{13}$C NMR δ. 7.33, 14.05, 18.35, 18.37, 22.00, 23.52, 24.26, 24.93, 31.02, 35.74, 40.52, 66.87, 69.99 (×2C), 73.33, 125.10, 125.13, 136.56, 167.29.

Example 3'

Synthesis of 2-((3-methacryloyloxy)-2,2-dimethyl-propoxy)methyl)-2-ethylhexyl methacrylate (NBDM)

In a glass reactor provided with a stirrer, a thermometer, a Vigreux column, and a Dean-Stark apparatus, 2-ethyl-2-(3-hydroxy-2,2-dimethyl-propoxymethyl)-hexan-1-ol (20.0 g, 81 mmol), methacrylic acid (17.8 g, 200 mmol), p-toluenesulfonic acid monohydrate (750 mg, 4 mmol), p-methoxyphenol (90 mg, 0.7 mmol), and cyclohexane (25 g) were mixed together. The mixture was warmed at an internal temperature of 90 to 105° C. and stirred under heating for 10 hours while water was distilled away from the system through azeotroping with cyclohexane. Cyclohexane was continuously returned to the reactor. The catalyst, unreacted methacrylic acid, and the polymerization inhibitor were removed by washing with a basic aqueous solution, and cyclohexane was then distilled away under reduced pressure to afford the intended product (yield: 30.5 g, purity: 93.9%, 72 mmol, % yield: 96%). As a result of identification through the $^1$H NMR spectrum and the $^{13}$C NMR spectrum, the product obtained in Example 3' was confirmed to be a compound having the same structure as the product in Example 3.

The abbreviations and suppliers for the raw materials used in Examples and Comparative Examples are as follows.

NDA: neopentyl glycol diacrylate (manufactured by Tokyo Chemical Industry Co., Ltd.)

HDDA: 1,6-hexanediol diacrylate (manufactured by Tokyo Chemical Industry Co., Ltd.)

HDDM: 1,6-hexanediol dimethacrylate (manufactured by Tokyo Chemical Industry Co., Ltd.)

UV-3300B: bifunctional urethane acrylate oligomer, product name "Shikoh UV-3300B" (manufactured by Nippon Synthetic Chemical Industry Co., Ltd.)

HCPK: 1-hydroxycyclohexyl phenyl ketone (radical polymerization initiator, manufactured by Wake Pure Chemical Industries, Ltd.)

In the following Examples 4, 5, and 6, the diacrylate compounds synthesized in Examples 1, 2, and 3 were UV-cured in a single composition, and the physical properties were measured. In Comparative Examples 1 to 5, neopentyl glycol diacrylate (NDA), 1,6-hexanediol diacrylate (HDDA), dineopentyl glycol diacrylate (dNDA), 1,6-hexanediol dimethacrylate (HDDM), and, dineopentyl glycol dimethacrylate (dNDM) were UV-cured in the same manner, and the physical properties were measured.

Curing Shrinkage:

The specific gravity of a monomer before curing was measured, with a pycnometer, and the specific gravity of the cured sheet with 0.4 mm thickness was measured with an electronic densimeter (EW-300SG, manufactured by Alfa Mirage Co., Ltd.). The curing shrinkage was calculated as follows.

(curing shrinkage,%)=[{(specific gravity of cured product)−(specific gravity before curing)}/(specific gravity of cured product)]×100

Pencil Hardness:

For a cured sheet with 0.4 mm thickness, the pencil hardness was measured with a pencil hardness tester manufactured by COTEC CORPORATION in accordance with JIS K 5600-5-4. When a scratch was generated at the hardness 6B, the pencil hardness was represented as lower than 6B.

Resistance to Bending:

For a thin-film cured sheet with 50 µm film thickness obtained by curing on a polycarbonate with 0.5 mm thickness as a base sheet material, the cured film was bent to an angle of 180° with a cylindrical mandrel bend tester manufactured by COTEC CORPORATION in accordance with XS K 5600-5-1, and the presence/absence of a crack or peeling-off was checked visually. The maximum diameter of the mandrel at which a crack or peeling-off was generated was recorded.

Curling Properties:

After obtaining a cured film with 50 µm film thickness by curing on a polycarbonate film with 100 µm thickness (product name "Iupilon Film FE-2000", manufactured by MITSUBISHI GAS CHEMICAL COMPANY, INC.), the polycarbonate film with the cured film was cut into a 100 mm×100 mm test piece. The test piece was placed on a horizontal plate and a curling height from the plate surface was measured at the four corners of the test piece. The average value of the curling heights at the four corners was recorded as the measurement.

Example 4

To NBDA (4.5 g) manufactured in Example 1, 5% by mass (225 mg) of 1-hydroxycyclohexyl phenyl ketone (HCPK) as a polymerization initiator was added, and dissolved therein homogeneously. The resultant was degassed with a vacuum pump to prepare a monomer composition. The monomer composition obtained was cured in accordance with the following method.

1) A glass sheet with 1 mm thickness, a PET film with 100 thickness, and a SUS mold with 0.4 mm thickness from which an area of 50 mm×50 mm had been hollowed out were stacked in the order presented, and the monomer composition was cast into the SUS mold. A PET film and a glass sheet were further stacked thereon, and the resultant was fixed and cured through irradiation with an ultraviolet ray.

2) The monomer composition was applied in a film thickness of 50 µm onto a polycarbonate sheet with 0.5 mm thickness with a bar coater, and cured through irradiation with an ultraviolet ray.

3) In the same manner as in 2), the monomer composition was applied in a film thickness of 50 µm onto a polycarbonate sheet with 100 µm thickness, and cured through irradiation with an ultraviolet way.

Physical properties were measured for the cured product obtained, and it was found that the curing shrinkage, the resistance to bending, the curling properties, and the pencil hardness were 7.0%, 4 mm, 7.5 mm, and 2H, respectively.

Example 5 and Comparative Examples 1, 2, and 3

To each of NMDA manufactured in Example 2, neopentyl glycol diacrylate (NDA), 1,6-hexanediol diacrylate (HDDA), and dineopentyl glycol diacrylate (dNDA) synthesized in the same manner as in Example 1, 5% by mass of HCPK as a polymerization initiator was added, and preparation of a monomer composition, production of a cured product, and measurement of physical properties were carried out in the same manner as in Example 4.

The evaluation results for the samples obtained by blending at a mass ratio, of diacrylate:polymerization initiator=100:5 followed by curing are shown in Table 1.

TABLE 1

|  | Example 4 | Example 5 | Comparative Example 1 | Comparative Example 2 | Comparative Example 3 |
| --- | --- | --- | --- | --- | --- |
| Diacrylate | NBDA | NMDA | NDA | HDDA | dNDA |
| Curing shrinkage (%) | 7.0 | 9.6 | 13.1 | 14.6 | 9.5 |
| Resistance to bending (mm) | 4 | 6 | >32 | 25 | 12 |
| Curling properties (mm) | 7.5 | 13.2 | 31.1 | 31.8 | 13.1 |
| Pencil hardness | 2H | 2H | 6H | 6H | 2H |

As shown in Table 1, the diacrylates in Examples 4 and 5 according to the present invention each exhibited satisfactory physical properties for all evaluation items of curing shrinkage, resistance to bending, curling properties, and pencil hardness, and provided a well-balanced cured product.

Example 6 and Comparative Examples 4 and 5

To each of NBDM manufactured in Example 3, 1,6-hexanediol dimethacrylate (HDDM), and dineopentyl glycol dimethacrylate (dNDM) synthesized in the same manner as in Example 3, 5% by mass of HCPK as a polymerization initiator was added, and preparation of a monomer composition, production of a cured product, and measurement of physical properties were carried out in the same manner as in Example 4.

The evaluation results for the samples obtained by blending at a mass ratio of dimethacrylate:polymerization initiator=100:5 followed by curing are shown in Table 2.

TABLE 2

|  | Example 6 | Comparative Example 4 | Comparative Example 5 |
|---|---|---|---|
| Dimethacrylate | NBDM | HDDM | dNDM |
| Curing shrinkage (%) | 9.1 | 15.2 | 11.2 |
| Resistance to bending (mm) | 10 | >32 | 25 |
| Curling properties (mm) | 6.0 | 22.1 | 16.2 |
| Pencil hardness | B | 5H | H |

As shown in Table 2, the dimethacrylates in Comparative Examples 4 and 5 each had a large curing shrinkage and were poor in resistance to bending and curling properties, and the dimethacrylate according to the present invention, on the other hand, had a small curing shrinkage, satisfactory resistance to bending, and low curling properties.

In the following Examples 7 and 8, a composition of the diacrylate synthesized in Examples 1 and 2 and a urethane acrylate oligomer (product name "Shikoh UV-3300B", manufactured by Nippon Synthetic Chemical Industry Co., Ltd., pencil hardness: lower than 6B) was cured, and physical properties were measured for the cured product. In Comparative Examples 6 and 7, a composition was similarly cured for NDA and HDDA, and physical properties were measured for the cured product.

Adhesion:

A thin-film cured sheet with 50 μm film thickness obtained by curing on a polycarbonate with 0.5 mm thickness as a base sheet material was evaluated by using a cross-cut tape method in accordance with JIS K 5400-8-5-2 with a cross-cut guide manufactured by COTEC CORPORATION. The degree of peeling in 100 cells was measured. The evaluation result is shown as (number of unpeeled cells)/100.

Example 7

In a water bath at 60° C., 29 g of NBDA manufactured in Example 1 and 2.9 g of a urethane acrylate oligomer were dissolved and homogenized. Thereto, 290 mg of HCPK was added and dissolved, and the resultant was degassed with a vacuum pump to prepare a composition. The composition was cured in the same manner as in Example 4, and physical properties were measured for the cured product obtained, and it was found that the pencil hardness, resistance to bending, curling properties, and a adhesion were lower than 6B, less than 3 mm, less than 0.5 mm, and 100/100, respectively.

Example 8 and Comparative Examples 6 and 7

Each of NMDA manufactured in Example 2, NDA, and HDDA was mixed with a urethane acrylate oligomer at a ratio to be described later and homogenized. Thereto, 5% by mass of HCPK as a polymerization initiator based on the total amount of the resin was added, and preparation of a resin composition, production of a cured product, and measurement of physical properties were carried Out in the same manner as in Example 7.

The evaluation results for the cured products obtained by blending at a mass ratio of diacrylate:urethane acrylate oligomer:polymerization initiator=50:50:5 followed by curing are shown in Table 3.

TABLE 3

|  | Example 7 | Example 8 | Comparative Example 6 | Comparative Example 7 |
|---|---|---|---|---|
| Diacrylate | NBDA | NMDA | NDA | HDDA |
| Pencil Hardness | lower than 6B | lower than 6B | B | B |
| Resistance to bending (mm) | <3 | <3 | <3 | 5 |
| Curling properties (mm) | <0.5 | <0.5 | 13.1 | 13.1 |
| Adhesion | 100/100 | 100/100 | 100/100 | 100/100 |

As shown in Table 3, in the case that a composition of a urethane acrylate oligomer, which is characterized by flexibility and high adhesion, and the diacrylate according to the present invention was wed as in Examples 7 and 8, the flexibility character of the urethane acrylate oligomer was maintained and a cured product having low curling properties and satisfactory adhesion was obtained, in contrast to Comparative Examples, in which a large curling occurred and the flexibility of the urethane acrylate oligomer was largely deteriorated.

INDUSTRIAL APPLICABILITY

As described above, the diacrylate compound represented by the formula (1) according to the present invention is characterized by providing a cured product having a good balance of physical properties such as low curing shrinkage, high resistance to bending, and low curling properties.

In addition, the diacrylate compound can be used for various curable resin compositions, and provides a cured product having a good balance of physical properties such as to curing shrinkage, high resistance to bending, and low curling properties.

The diacrylate compound represented by the formula (1) according to the present invention, which is characterized as described above, and the composition containing the diacrylate compound can be used, for example, as a reactive diluent or a viscosity modifier for various applications such as coating materials, coating agents, hard coating agents, inks, adhesives, pressure-sensitive adhesives, resists, molding materials, and surface treatment agents.

The invention claimed is:

1. A di(meth)acrylate compound of formula (1):

(1)

wherein

R denotes a hydrogen atom or a methyl group; and $R^1$, $R^2$, $R^3$, and $R^4$ each independently denote a $C_{1-6}$ linear or branched alkyl group, with the proviso that $R^1$, $R^2$, $R^3$, and $R^4$ are not all methyl groups, and wherein a combination of an alkyl group denoted as $R^1$ and an alkyl group denoted as $R^2$ is different from a combination of an alkyl group denoted as $R^3$ and an alkyl group denoted as $R^4$.

2. The diacrylate compound according to claim 1, wherein, in the formula (1), $R^1$ and $R^2$ are each a methyl group.

3. A composition comprising: the diacrylate compound according to claim 1; and at least one selected from the group consisting of an additional polymerizable monomer, a polymerizable oligomer, and a radical polymerization initiator.

4. The composition according to claim 3 comprising a radical polymerization initiator.

5. The composition according to claim 3 comprising a photo-radical polymerization initiator.

6. The composition according to claim 3 comprising at least one selected from the group consisting of a urethane acrylate oligomer and a urethane methacrylate oligomer.

7. A cured product obtained by curing the composition according to claim 3.

8. An adhesive comprising the composition according to claim 3.

9. An ink comprising the composition according to claim 3.

10. A coating material comprising the composition according to claim 3.

* * * * *